United States Patent [19]
Uchiyama et al.

[11] Patent Number: 5,789,446
[45] Date of Patent: Aug. 4, 1998

[54] THERAPEUTIC AGENT FOR TREATING JOINT DISEASES ASSOCIATED WITH ARTHRITIS

[75] Inventors: Akiyoshi Uchiyama, Tokyo; Kenzo Muramoto, Ibaraki; Kenichi Chiba, Ibaraki; Takashi Yamanaka, Ibaraki; Isao Yamatsu, Ibaraki, all of Japan

[73] Assignee: Eisai Co., Ltd., Tokyo, Japan

[21] Appl. No.: 877,459

[22] Filed: Jun. 17, 1997

[30] Foreign Application Priority Data

Jun. 17, 1996 [JP] Japan ................... 8-155661

[51] Int. Cl.$^6$ ........................ A61K 31/19
[52] U.S. Cl. ........................ 514/568
[58] Field of Search ................ 514/568

[56] References Cited

U.S. PATENT DOCUMENTS 5,385,942  1/1995  Abe et al. .................. 514/568

OTHER PUBLICATIONS

Rakel, "Conn's Current Therapy", published by W.B. Saunders Company, (PA), pp. 913–917 and 928–931, 1992.

*Primary Examiner*—Raymond Henley, III

*Attorney, Agent, or Firm*—Flynn, Thiel, Boutell & Tanis, P.C.

[57] ABSTRACT

To provide a treating or ameliorating agent for joint diseases accompanied with arthritis, preferably, a rheumatoid arthritis or ameliorating agent, which exerts excellent pharmaceutical effects. The active ingredient is a quinone derivative represented by the following general formula (I) or pharmacologically acceptable salts thereof:

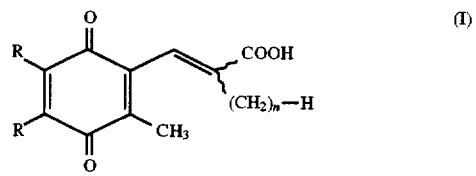

wherein n is 0 or an integer of 1 to 12 and R is a methyl or methoxy group.

5 Claims, 10 Drawing Sheets

THERAPEUTIC AGENT FOR TREATING JOINT DISEASES ASSOCIATED WITH ARTHRITIS

BACKGROUND OF THE INVENTION

The present invention relates to a preventing, curing or ameliorating agent for joint diseases associated with arthritis, which exhibits excellent functions as a medicine, and preferably relates to a rheumatoid arthritis preventing, curing or ameliorating agent.

The joint diseases are roughly classified into arthrosis deformans accompanying traumatic deformation or regressive degeneration caused by aging, polyarthritis accompanying desmosis and the noncausal monarthritis/polyarthritis. A representative example of the desmosis arthritis is rheumatoid arthritis. Although the above arthropathy or arthritis does not directly cause death, the destruction of cartilage and bone would be promoted thereby with the passage of time so as to cause pain with the result that functional disorders of limbs would be invited. Thus, the arthropathy or arthritis is a disease which exerts a great influence on daily living.

PRIOR ART

The treatment of rheumatoid arthritis or other arthritides varies depending on the severity and progress thereof.

For light and early cases, use is made of nonsteroidal antiinflammatory drugs (hereinafter referred to as NSAIDs") for pain relief. On the other hand, for medium or severe cases, use is also made of adrenocorticosteroidal agents. Especially, disease-modifying antirheumatic agents (hereinafter referred to as "DMARDs", including immunosuppressive agents) are administered to cases with desmotic arthritides such as rheumatoid arthritis. It is typical that a plurality of drugs mentioned above are administered in accordance with the symptoms for medium to severe cases.

More specifically, representative examples of NSAIDs include those of a relatively short blood half-time such as aspirin, ibuprofen, roxoprofen, diclofenac and indometacin, those of medium blood half-time such as naproxen, sulindac, fenbufen and diflunisal and those of long blood half-time such as piroxicam, oxaprozin and tenoxicam.

Representative examples of DMARDs include gold preparations, D-penicillamine, bucillamine, lobenzarit, sulfasalazine, actarit and immunosuppressive agents (e.g., mizoribine, methotrexate, azathioprine, cyclophosphamide and cyclosporin).

Representative examples of adrenocorticosteroidal agents include betamethasone, prednisolone and dexamethasone.

With respect to the cause of the joint diseases associated with arthritides such as rheumatoid arthritis, it is believed that an immune anomaly is greatly associated therewith. However, there still remain many unclear points and the current situation is that there is no radical method of treatment. The currently employed treating method is mainly one of the symptomatic therapy type, by which it is difficult to suppress the progress of articular rupture, which is a crucial problem of arthritides.

Now, only seven pharmaceutical preparations, i.e., parenteral gold preparation (aurothiomalate sodium), oral gold preparation (auranofin), D-penicillamine, lobenzarit, bucillamine, mizoribine and actarit are officially permitted on the administration for treating rheumatoid arthritis. Although there are cases which have exhibited a significant suppression of articular rupture, many cases exhibit no effect of these pharmaceutical preparations and these preparations have been unable to give a therapy satisfactory for all of the cases.

Further, the use of NSAIDs causes a multiplicity of digestive-system-related side effects such as gastric ulcer, among which side effects such as hepatorenal disorder and central nerve disorder (anxiety, insomnia, sleepiness, etc.) are also recognized. Thus, a combined use of an antiulcer agent and a periodic examination are needed and a long-term chronic administration of NSAIDs has involved many problems.

With respect to DMARDs, they are ineffective in numerous cases and three to four months are taken before the development of any effect. Thus, the problem has existed that, even in light cases, lesion progresses during that period. Moreover, even effective cases occasionally encounter the escape phenomenon such that the effect is diminished two to three years after use, and side effects such as anthema, interstitial pneumonia, renal disorder and hematopoietic organ disorder have been common problems.

Adrenocorticosteroidal agents (e.g., betamethasone, prednisolone and dexamethasone) are likely to induce numerous side effects such as infectious disease induction attributed to immune degradation, endocrine anomaly, skin pigmentation and tendency toward osteoporosis when administered for a prolonged period of time. Thus, careful observation has been required for the long-term administration thereof.

As apparent from the above, the current situation is that there is no radical therapeutic agent for joint diseases such as arthritis and rheumatoid arthritis. Furthermore, numerous safety problems have been involved. Therefore, there is a demand for a novel joint disease preventing, curing or ameliorating agent.

DETAILED DESCRIPTION

Therefore, the inventors have conducted various studies with a view toward developing a clinically highly effective and highly safe therapeutic agent for arthritides, for example, rheumatoid arthritis, which approaches a radical therapy. As a result, it has been found that the below described quinone derivative represented by the general formula (I) can attain the intended object and the present invention has been completed. The quinone derivative (I) of the present invention is characterized by having both an excellent antiarthritic effect and safety and, hence, the value of the present invention is very high.

The present invention provides a method for preventing, curing or ameliorating joint diseases associated with arthritis, comprising administering a pharmacologically effective amount of a quinone derivative represented by the following general formula (I) or a pharmacologically acceptable salts thereof, to a person suffering from the joint diseases associated with arthritis.

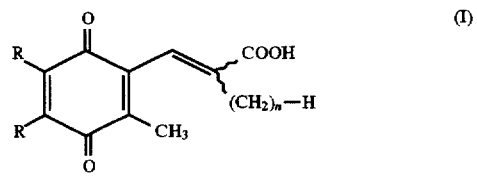

wherein n is 0 or an integer of 1 to 12 and R is a methyl or methoxy group.

The present invention further provides the method, wherein the joint disease associated with arthritis is rheumatoid arthritis.

The present invention further provides the method, wherein the quinone derivative (I) is (E)-3-[2-(5,6-dimethoxy-3-methyl-1,4-benzoquinonyl)]-2- nonylpropenoic acid represented by the following chemical formula (II):

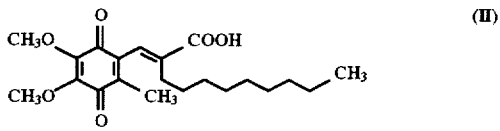

The present invention provides a method for preventing, curing or ameliorating rheumatoid arthritis, comprising administering a pharmacologically effective amount of a quinone derivative represented by the above shown general formula (II), or a pharmacologically acceptable salts thereof, to a person suffering from the rheumatoid arthritis.

The present invention provides for the use of a quinone derivative represented by the following general formula (I), or a pharmacologically acceptable salt thereof, for manufacturing a preventing, curing or ameliorating agent for joint diseases accompanied with arthritis.

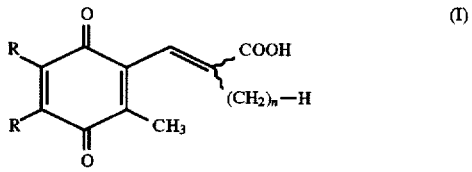

wherein n is 0 or an integer of 1 to 12 and R is a methyl or methoxy group.

The quinone derivative (I) of the present invention is represented by the following general formula:

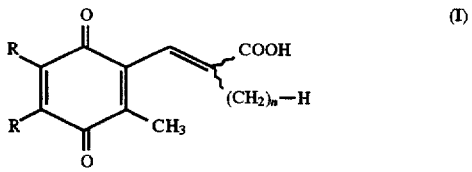

In the formula, n is 0 or an integer of 1 to 12 and R is a methyl or methoxy group.

The quinone derivative (I) of the present invention has double bonds in its molecule, so that there are geometrical isomers. The geometrical isomers are not limited in the present invention, and the quinone derivative (I) may be in the form of either a single isomer (E-isomer or Z-isomer) selected from among the isomers or a mixture of two or more of isomers (EZ mixture). Moreover, the quinone derivative (I) may be formed into a hydrate.

The pharmacologically acceptable salts of the present invention are not limited as long as they are in the form of an addition salt of the quinone derivative (I) of the present invention. Examples thereof include alkali metal addition salts such as sodium, potassium and lithium salts, alkaline earth metal addition salts such as magnesium and calcium salts, amine addition salts and amino acid addition salts.

The following compounds can be mentioned as specific examples of the quinone derivatives (I), to which the present invention is not limited. (1) 3-[2-(5,6-dimethoxy-3-methyl-1,4-benzoquinonyl)]-propenoic acid; (2) 3-[2-(5,6-dimethoxy-3-methyl-1,4-benzoquinonyl)]-2-propylpropenoic acid; (3) 3-[2-(5,6-dimethoxy-3-methyl-1,4-benzoquinonyl)]-2-hexylpropenoic acid; (4) 3-[2-(5,6-dimethoxy-3-methyl-1,4-benzoquinonyl)]-2-nonylpropenoic acid; (5) 3-[2-(5,6-dimethoxy-3-methyl-1,4-benzoquinonyl)]-2-dodecylpropenoic acid; (6) 3-[2-(3,5,6-trimethyl-1,4-benzoquinonyl)]propenoic acid; (7) 3-[2-(3,5,6-trimethyl-1,4-benzoquinonyl)]-2-propylpropenoic acid; (8) 3-[2-(3,5,6-trimethyl-1,4-benzoquinonyl)]-2-hexylpropenoic acid; (9) 3-[2-(3,5,6-trimethyl-1,4-benzoquinonyl)]-2-nonyl-propenoic acid and (10) 3-[2-(3,5,6-trimethyl-1,4-benzoquinonyl)]-2-dodecylpropenoic acid.

Of these quinone derivatives (I), 3-[2-(5,6-dimethoxy-3-metyl-1,4-benzoquinonyl)]-2-nonylpropenoic acid is preferred, and (E)-3-[2-(5,6-dimethoxy-3-methyl-1,4-benzoquinonyl)]-2-nonylpropenoic acid represented by the following chemical formula (II) is more preferred:

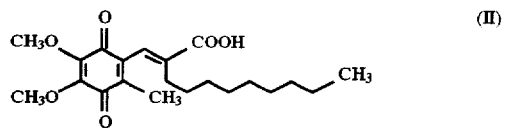

The quinone derivative (I) of the present invention can be prepared by the process described in EP-A 419905.

Dosage forms of the compound of the present invention are, for example, oral preparations such as powders, fine granules, granules, tablets, coated tablets and capsules, external preparations such as ointments and patches, suppositories, creams, lotions and injections. Such pharmaceutical preparations can be prepared with the use of commonly accepted carriers for pharmaceutical preparations in accordance with the customary procedures.

Specifically, for producing an oral preparation, the compound of the present invention is blended with an additive and, if necessary, an antioxidant, a binder, a disintegrator, a lubricant, a coloring agent, a corrigent, etc., followed by formation of powders, fine subtilaes, granules, tablets, coated tablets or capsules in accordance with the customary procedure.

Examples of the additives include lactose, corn starch, sucrose, glucose, mannitol, sorbitol, crystalline cellulose and silicon dioxide. Examples of the binders include polyvinyl alcohol, polyvinyl ether, methylcellulose, ethylcellulose, acacia, tragacanth, gelatin, shellac, hydroxypropyl-methylcellulose, hydroxypropylcellulose, polyvinylpyrrolidone, polypropylene glycol/polyoxyethylene block copolymer and meglumine. Examples of the disintegrators include starch, agar, gelatin powder, crystalline cellulose, calcium carbonate, sodium bicarbonate, calcium citrate, dextrin, pectin and calcium carboxymethylcellulose. Examples of the lubricants include magnesium stearate, talc, polyethylene glycol, silica and hydrogenated vegetable oil. Any colorant of which its addition to pharmaceuticals is officially allowed can be used as the colorant. Examples of the corrigents include cacao powder, menthol, aromatic powder, mentha oil, borneol and powdered cinnamon bark. It is a matter of course that a sugar coating and, if necessary, suitable other coatings may be applied on these tablets and granules.

For producing an injection, the compound of the present invention is loaded with a pH modifier, a solubilizing agent, a tonicity agent, etc. and, if necessary, a solubilizing auxiliary, a stabilizer, an antioxidant, etc., followed by processing into an injection form in accordance with the customary procedure.

The process for producing external preparations is not limited, and they can be produced by conventional methods. In the production of external preparations, various materials customarily employed in pharmaceutical preparations, quasi-drugs, cosmetics, etc. can be used as the base material.

Examples of the employed base materials include animal and vegetable oils, mineral oils, ester oils, waxes, higher alcohols, fatty acids, silicone oils, surfactants, phospholipids, alcohols, polyhydric alcohols, water soluble polymers, clay minerals and purified water. Further, according to necessity, a pH modifier, an antioxidant, a chelating agent, an antiseptic/fungicide, a colorant, a perfume, etc. can be added to the above, though the base materials of the external preparations of the present invention are not limited to these materials. Still further, according to necessity, a blood flow promoter, a bactericide, an antiinflammatory agent, a cell activator, a vitamin, an amino acid, a humectant, a keratolytic agent and other ingredients can be added to the external preparations. Each of the above base materials is added in such an amount that the desired concentration in the production of common external preparations is realized.

The clinical dose of the quinone derivative (I) of the present invention, or pharmacologically acceptable salts thereof, is not limited and varies depending on the symptom, severity, age and complication and further depends on the type of salt, route of administration, etc. However, in general, the daily dose ranges from 0.01 to 2000 mg, preferably, from 0.1 to 1000 mg and, still preferably, from 1 to 500 mg per adult, which is given orally, intravenously, intramuscularly, per rectum or percutaneously.

The efficacy of the compound of the present invention as an arthritis preventing, curing or ameliorating agent will be demonstrated with reference to the following Pharmacological Experiment and Toxicity Test Examples, which in no way limit the scope of the compounds of the present invention and the use thereof.

EXAMPLES

Pharmacological Experiment Example (Experimental Method)

Figure 1:
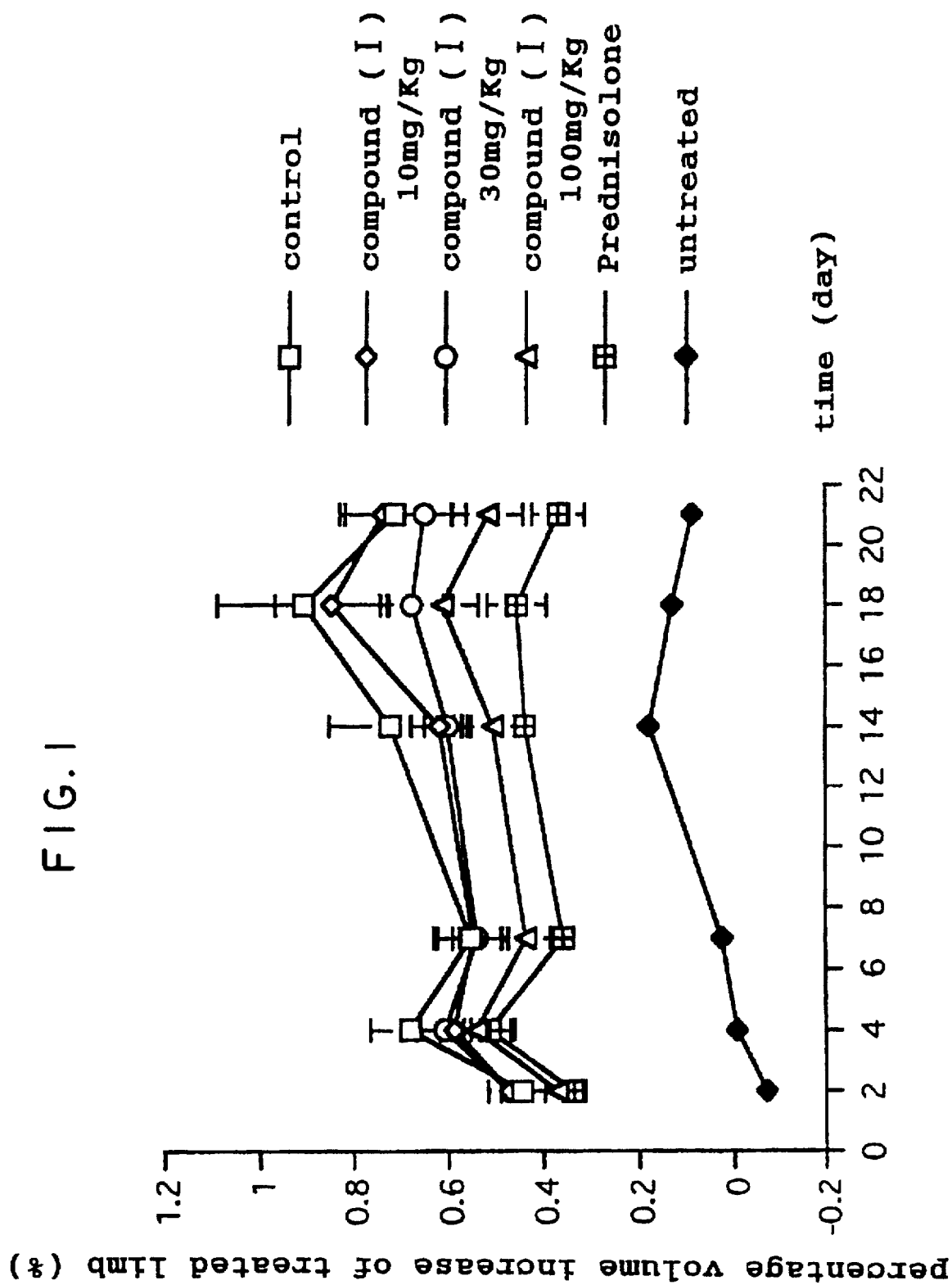
FIG. 1 is a graph showing the change with the passage of time of the percentage volume increase a of treated limb in the group dosed with the compound of the present invention, the positive control group (prednisolone) and the control group (average ± standard error).

(E)-3-|2-(5,6-Dimethoxy-3-methyl-1,4-quinonyl)|-2-nonylpropenoic acid as a representative example of the quinone derivative (I) of the present invention (hereinafter referred to simply as "compound (I)") was used as a test compound and prednisolone was used as a positive control.
(1) Animal grouping:

Forty-eight 6 to 7-week old F344 male rats having undergone 1 to 2-week preliminary breeding were randomly divided into six groups specified in the following Table.

| Group No. | Test compd. | Dose | No. of cases |
|---|---|---|---|
| 1 | control | 0.5% methylcellulose (10 ml/kg) | 8 |
| 2 | compd. (I) | 10 mg/kg | 8 |
| 3 | compd. (I) | 30 mg/kg | 8 |
| 4 | compd. (I) | 100 mg/kg | 8 |
| 5 | Prednisolone | 5 mg/kg | 8 |
| 6 | untreated | | 8 |

(2) Administration method and conditions:

Each administration specimen was prepared in the following manner.

1) Control (0.5% methylcellulose solution):

5 g of methylcellulose was weighed out, and 800 ml of distilled water was added to thereby dissolve the same. The solution was measured up to 1000 ml. The resultant 0.5% methylcellulose solution was divided into about 200 ml portions, well stoppered, sterilized at 121° C. for 15 min and preserved at room temperature. After the unstoppering, they were preserved at 4° C.

2) Compound (I):

300 to 600 mg of the compound (I) was placed in a mortar and suspended by adding the 0.5% methyl-cellulose solution little by little. The obtained suspension was measured up with the use of the 0.5% methylcellulose solution so as to have a concentration of 100 mg/ml. The 100 mg/ml solution was diluted with the 0.5% methylcellulose solution in the manner specified in the following Table, thereby obtaining 30 mg/ml and 1 mg/ml suspensions.

| Suspension | Concn. | Feed liq. + 0.5% methylcellulose solution |
|---|---|---|
| A | 50 (mg/ml) | — |
| B | 15 | 15 to 20 ml liq. A + 7/3 times as much as liq. A added |
| C | 5 | 4 to 6 ml liq. A + 9 times as much as liq. B added |

Suspensions A, B and C were administered to Group Nos. 4 (100 mg/kg), 3 (30 mg/kg) and 2 (10 mg/kg), respectively. The stability of each suspension at 4° C. was separately confirmed over a period of one week. Each suspension was preserved at 4° C. for one week. A suspension whose preservation period exceeded one week was discarded and a new suspension was prepared therefor.

3) Prednisolone:

40 to 60 mg of prednisolone was placed in a mortar and suspended by adding the 0.5% methyl-cellulose solution little by little. The obtained suspension was measured up with the use of the 0.5% methylcellulose solution so as to have a concentration of 1 mg/ml. The stability of the suspension at 4° C. was separately confirmed over a period of one week. The suspension was preserved at 4° C. for one week. The suspension whose preservation period exceeded one week was discarded and a new suspension was prepared therefor.

Each test compound was suspended in the 0.5% methyl-cellulose solution, thereby obtaining suspensions of varied concentrations. Each of the suspensions was forcibly administered orally in a dose of 5 ml/kg by the use of a stainless steel sonde once a day for a period of 21 days. (3) Preparation of adjuvant and induction of arthritis:

1) Preparation of adjuvant:

100 mg of Mycobacterium. butyricum was put in a mortar and ground well. 10 ml of liquid paraffin was added thereto, mixed well and sterilized in an autoclave (120° C., 20 min).

2) Induction of arthritis:

50 μl of the thus prepared adjuvant was injected into the right hindlimb foot pad of each rat to thereby induce arthritis. (4) Experimental schedule:

The blood was collected and the spleen, thymus and adrenal gland were extirpated on the day following the termination of repeated administration. Various hematologic and inflammatory parameters were evaluated with the use of collected blood and each organ was weighed. (5) Pretreatment of animal:

Each animal was etherized prior to the blood collection. (6) Experimental operation:

1) Measurement items:

a) hematologic parameters: hematocrit value, hemoglobin level, red blood cell count and white blood cell count.

b) inflammatory parameters: erythrocyte sedimentation rate, ratio of albumin to globulin, sialic acid level and plasma fibrinogen level.

c) weight of organ.

2) Specimen collection and preparation:

a) Blood collection:

The abdomen was opened under etherization and the abdominal aorta was exposed. Blood was collected and, immediately thereafter, 1, 2 and 2 ml thereof were introduced into an EDTA blood collection tube, a plastic tube containing 250 μl of a 3.8% sodium citrate solution (Yamanouchi Pharmaceutical Co., Ltd., Tokyo) and a glass test tube, respectively. After the collection of about 5 ml of blood from the abdominal aorta and the introduction thereof into the tubes, an anticoagulant agent was mixed into the blood in each of the tubes.

b) organ collection:

After the blood collection, the spleen, thymus and adrenal gland were extirpated and the weights thereof were measured to calculate the organ weight per body weight.

3) Experimental method:

a) Measurement of volume of hindlimb:

The volume of each hindlimb was measured by plethysmography (TK-1 Unicom) and the volume increase rate was calculated by the following equation. The measurement obtained immediately after the injection of the adjuvant with respect to the treated limb and the measurement obtained 7 days after the injection (immediately before the onset of secondary inflammation) with respect to the untreated limb were taken as the normal values:

Volume increase rate=(measurement—normal value)/ (normal value).

b) Hematocrit value, hemoglobin level, red blood cell count and white blood cell count:

The red blood cell count (flow cytometric light scattering measurement), mean corpuscular volume (MCV, flow cytometric light scattering measurement), differential blood platelet count (flow cytometric light scattering measurement) and white blood cell count (peroxidase method, flow cytometric light scattering measurement) of EDTA-2K treated blood were measured by means of a blood diagnostic device (H-1 Techinicon Instruments Corp., U.S.A.) thereby calculating the hematocrit value (HCT) and mean corpuscular hemoglobin concentration (MCHC).

c) Ratio of albumin to globulin, sialic acid level and plasma fibrinogen level:

measured at Koto Biseibutsu Kenkyusho (Tsukuba City).

d) Erythrocyte sedimentation rate:

The blood was mixed well with the 3.8% sodium citrate solution in the plastic tube and put in a 2.5 ml syringe cylinder (TERUMO CORP.) and 1 ml thereof was injected into a blood sedimentation tube (Nitipet C, Nippon Rinsho Kikai Kogyo K.K., Tokyo). The erythrocyte sedimentation distance was measured 1 hr and 2 hr later to thereby determine the erythrocyte sedimentation rate.

e) Measurement of blood interleukin-6 (IL-6):

A bioassay was conducted with the use of cell B9 (cell which grows dependently on IL-6). Seven twofold-by-twofold serial dilutions starting, with a tenfold dilution of blood sera were made on a 96-well plate. Human recombinant IL-6 was used as the standard and a calibration curve was prepared by making nine twofold-by-twofold serial dilutions starting with 5 units/ml. Cell B9 was put in an amount of 1500 cells per 50 μl of specimen in each well and cultured in a $CO_2$ incubator for 3 days. Thereafter, MTT was dissolved in PBS (phosphate-buffered saline) in a proportion of 5 mg/ml and put in each well in an amount of 20 μl per well. One hour later, 10% SDS (sodium lauryl sulfate) was put in each well in an amount of 100 μl per well to effect dissolution. Thereafter, measurements were performed at two wavelengths, i.e., 540 and 660 nm with the use of a microtiter tray reader, and the IL-6 value was calculated from the remainder obtained by subtracting the measurement at 660 nm from the measurement at 540 nm.

4) Measuring instrument:

Use was made of a blood diagnostic device (H-1 Techinicon Instruments Co., U.S.A.), Microtiter Tray Reader (NJ-2000 by Nippon Intermed K.K., Tokyo) and plethysmography (TK-1 Unicom, U.S.A.).

(Results) All results are expressed by the average ± standard error.

1) Percentage volume increase (%) of treated limb (refer to FIG. 1)

| | | Test compd. | | | | |
|---|---|---|---|---|---|---|
| | | compd.(I) [mg/Kg] | | | Prednisolone | |
| week | control | 10 | 30 | 100 | 5 | untreated |
| 2 | 0.444 ± 0.047 | 0.472 ± 0.045 | 0.472 ± 0.044 | 0.370 ± 0.060 | 0.336 ± 0.036 | −0.070 ± 0.010 |
| 4 | 0.678 ± 0.084 | 0.586 ± 0.072 | 0.607 ± 0.055 | 0.541 ± 0.073 | 0.514 ± 0.054 | −0.006 ± 0.013 |
| 7 | 0.553 ± 0.077 | 0.548 ± 0.074 | 0.539 ± 0.051 | 0.436 ± 0.051 | 0.357 ± 0.038 | 0.025 ± 0.016 |
| 14 | 0.719 ± | 0.616 ± | 0.599 ± | 0.505 ± | 0.437 ± | 0.177 ± |

-continued

Test compd.

| week | control | compd.(I) [mg/Kg] 10 | 30 | 100 | Prednisolone 5 | untreated |
|---|---|---|---|---|---|---|
| | 0.132 | 0.059 | 0.048 | 0.065 | 0.037 | 0.016 |
| 18 | 0.906 ± 0.183 | 0.846 ± 0.121 | 0.674 ± 0.067 | 0.609 ± 0.073 | 0.455 ± 0.063 | 0.129 ± 0.024 |
| 21 | 0.710 ± 0.119 | 0.734 ± 0.083 | 0.648 ± 0.087 | 0.515 ± 0.073 | 0.366 ± 0.055 | 0.087 ± 0.015 |

Figure 2:
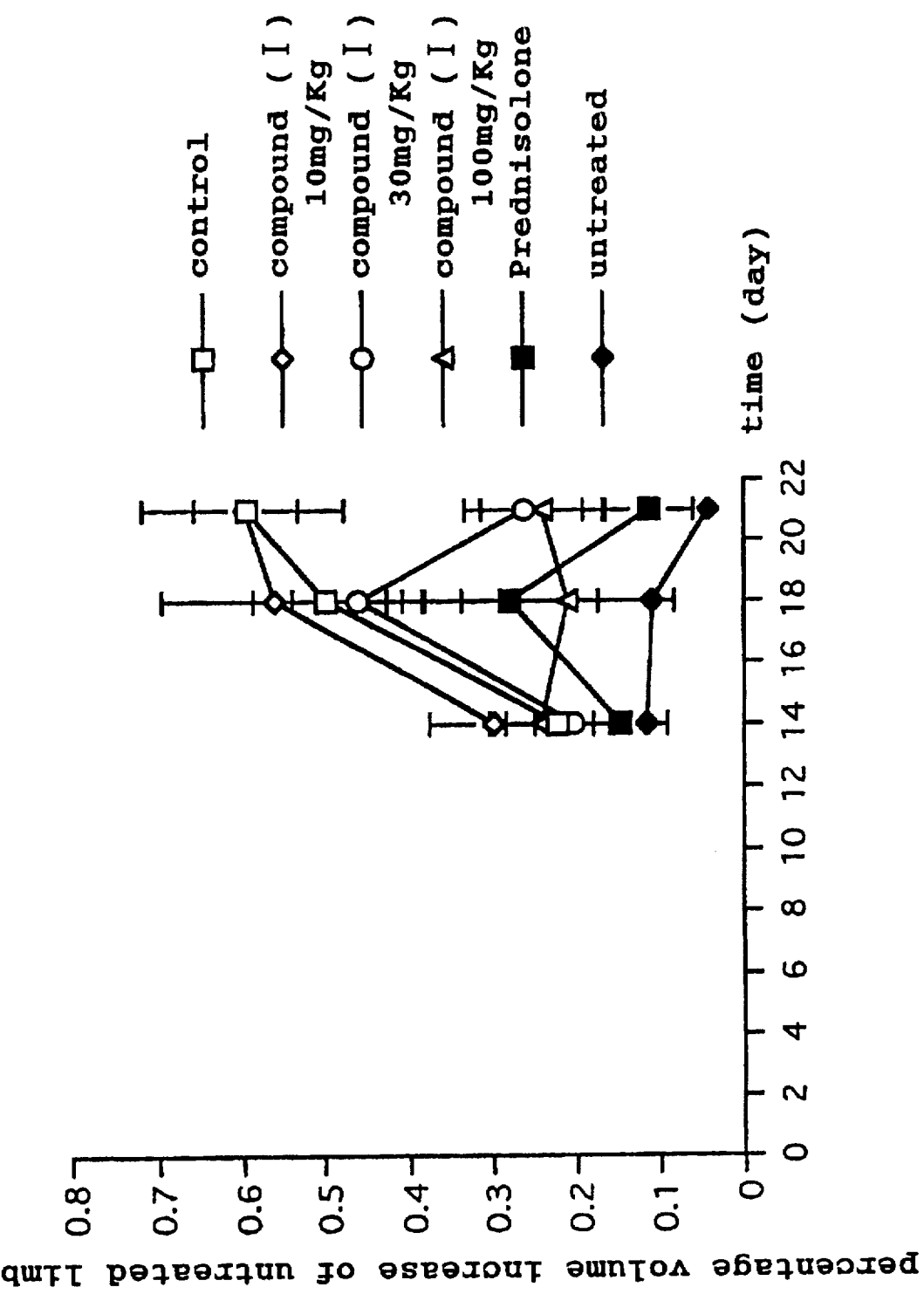
FIG. 2 is a graph showing the change with the passage of time of the percentage volume increase of an untreated limb in the group dosed with the compound of the present invention, the positive control group (prednisolone) and the control group (average ± standard error).
Figure 3:
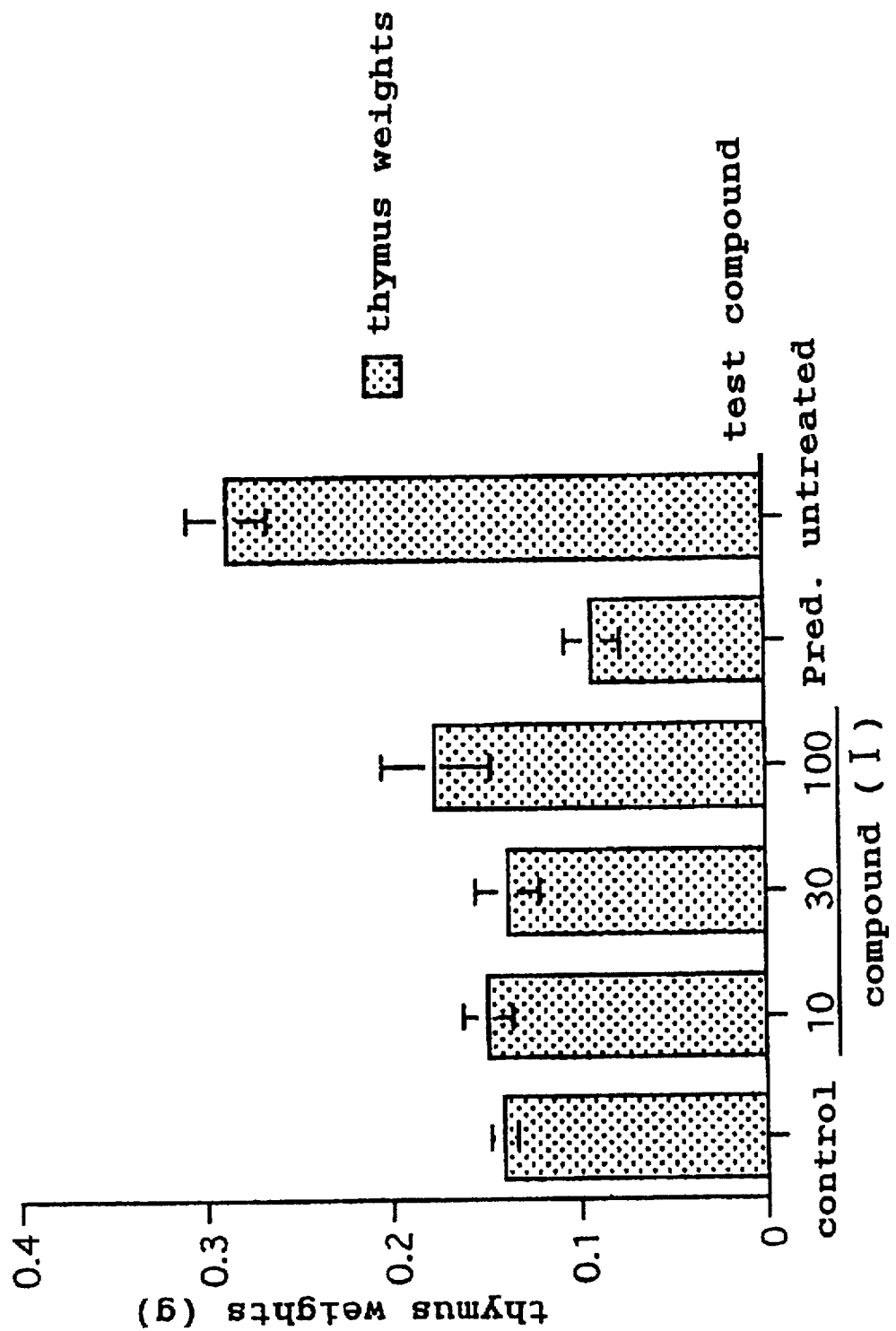
FIG. 3 is a graph comparing thymus weights among the group dosed with the compound of the present invention, the positive control group (prednisolone) and the control group (average ± standard error).
Figure 4:
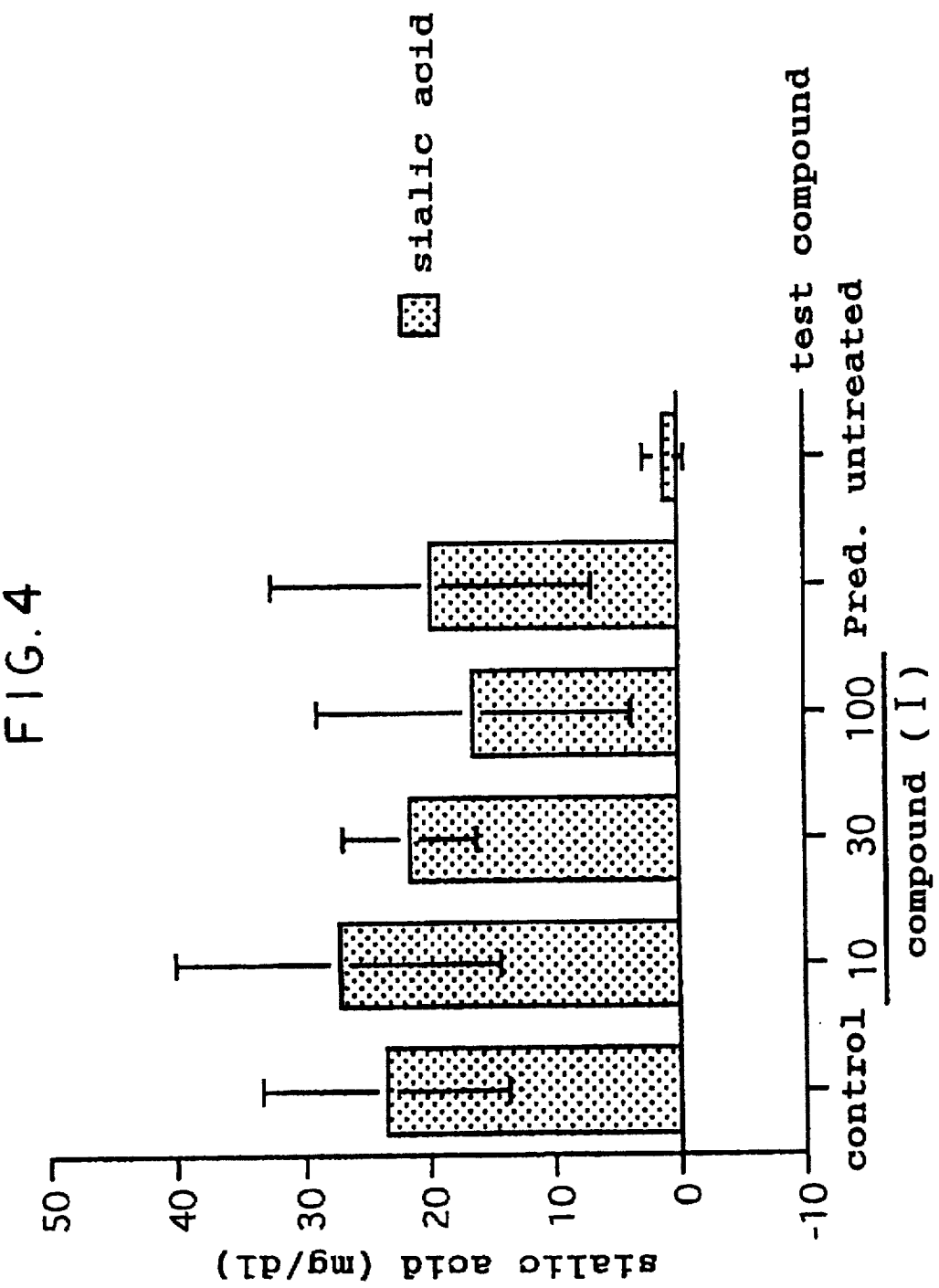
FIG. 4 is a graph comparing sialic acid levels among the group dosed with the compound of the present invention, the positive control group (prednisolone) and the control group (average ± standard error).
Figure 5:
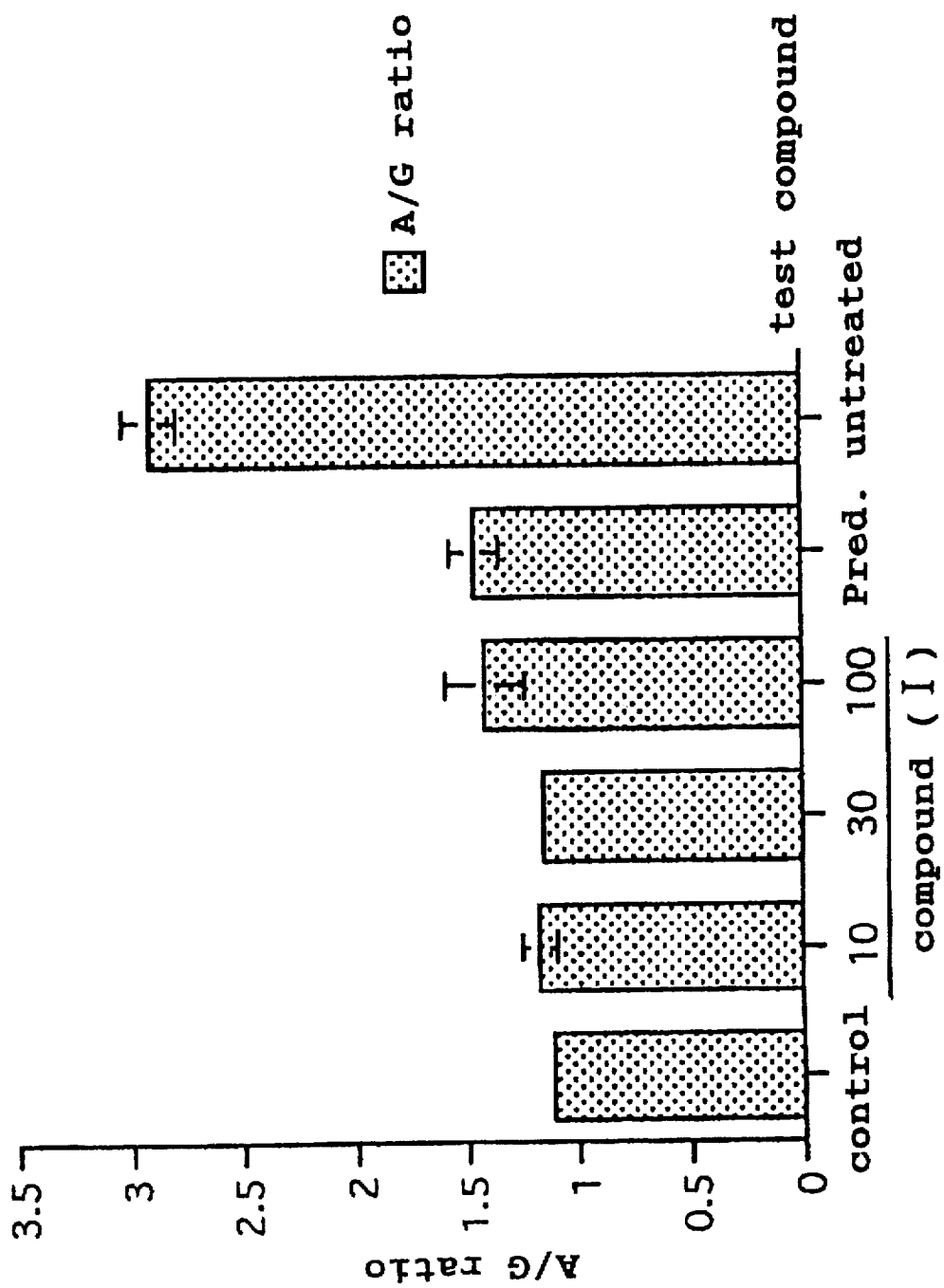
FIG. 5 is a graph comparing A/G ratios among the group dosed with the compound of the present invention, the positive control group (prednisolone) and the control group (average ± standard error).
Figure 6:
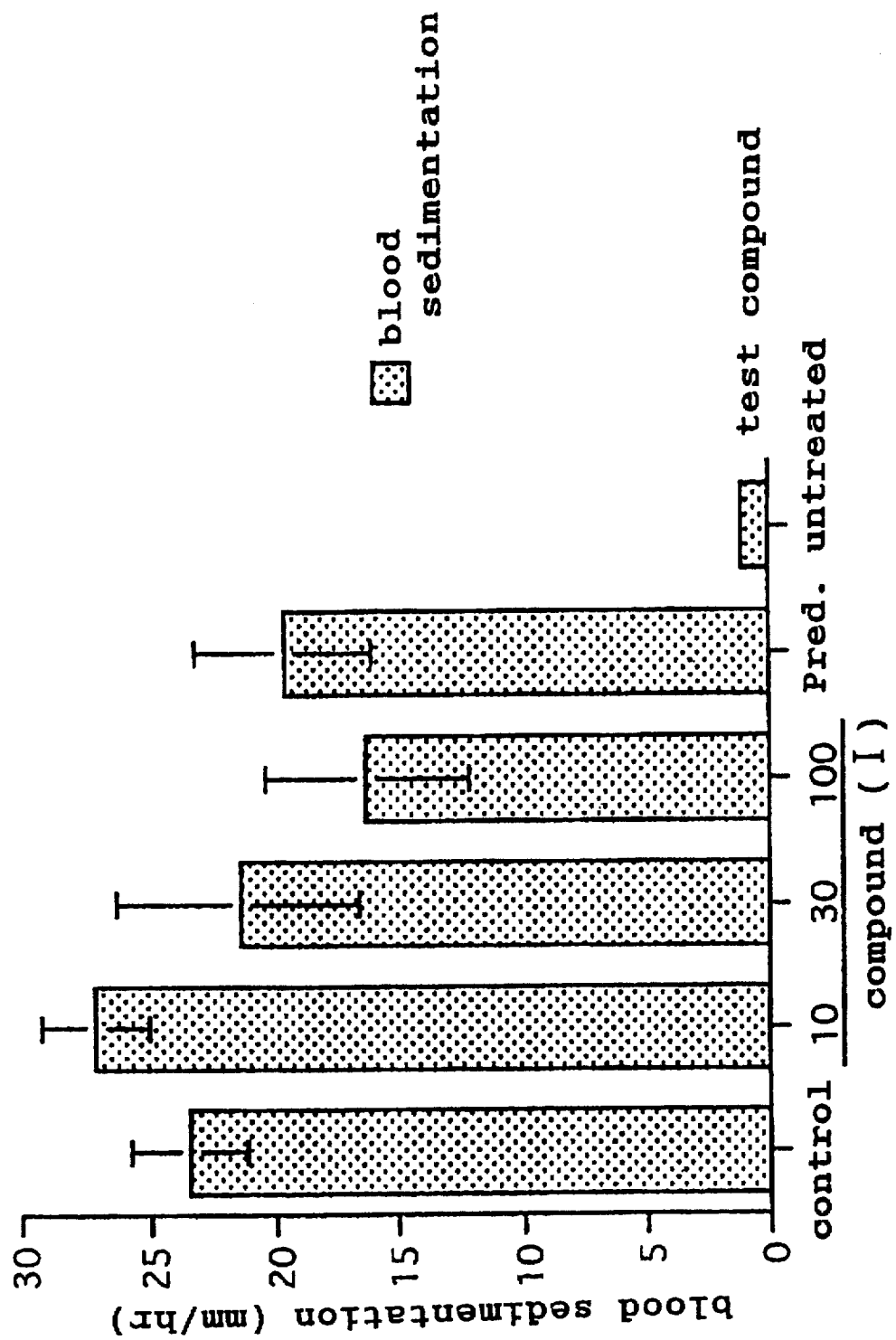
FIG. 6 is a graph comparing blood sedimentations among the group dosed with the compound of the present invention, the positive control group (prednisolone) and the control group (average ± standard error).
Figure 7:
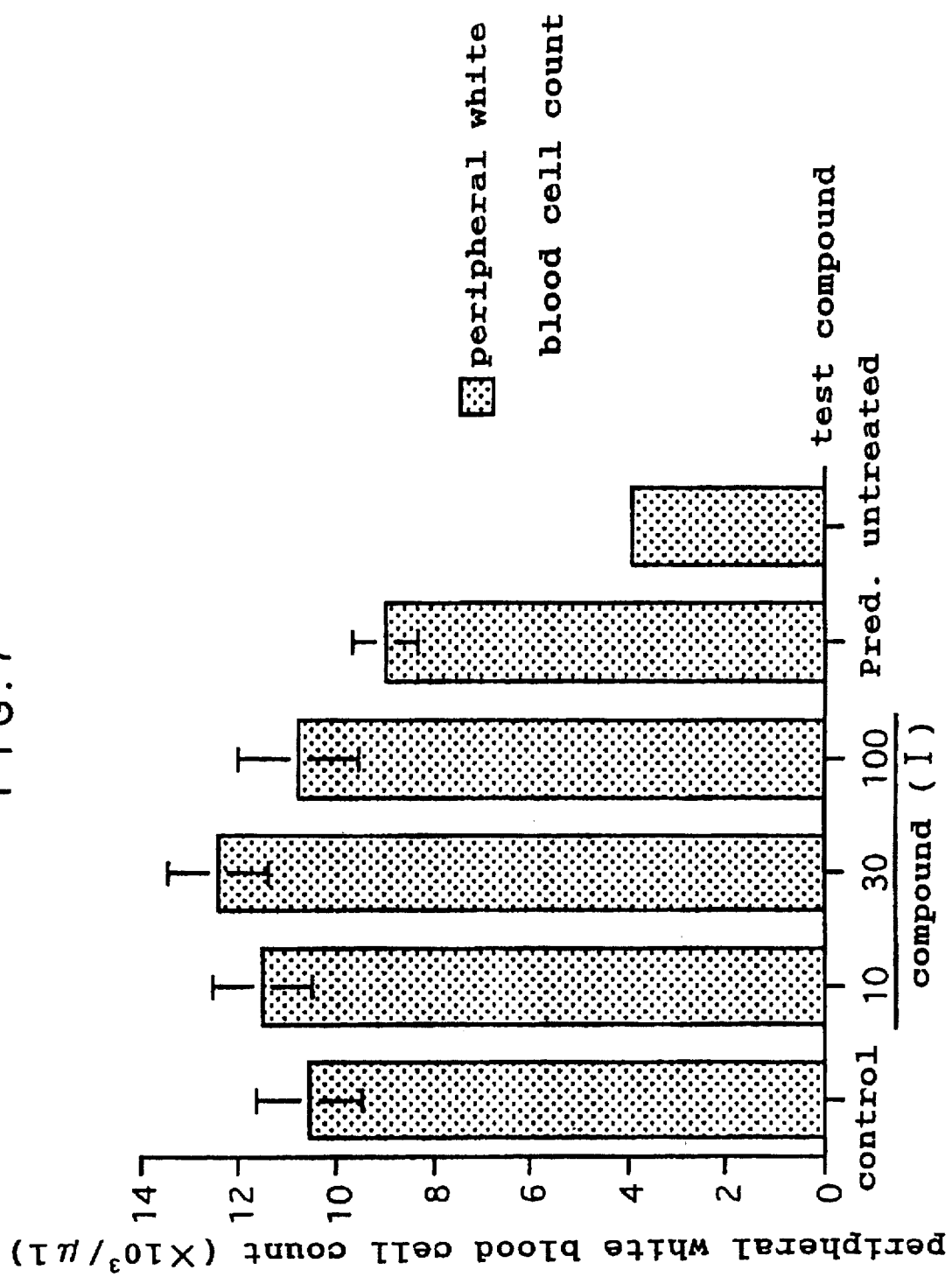
FIG. 7 is a graph comparing peripheral white blood cell counts among the group dosed with the compound of the present invention, the positive control group (prednisolone) and the control group (average ± standard error).
Figure 8:
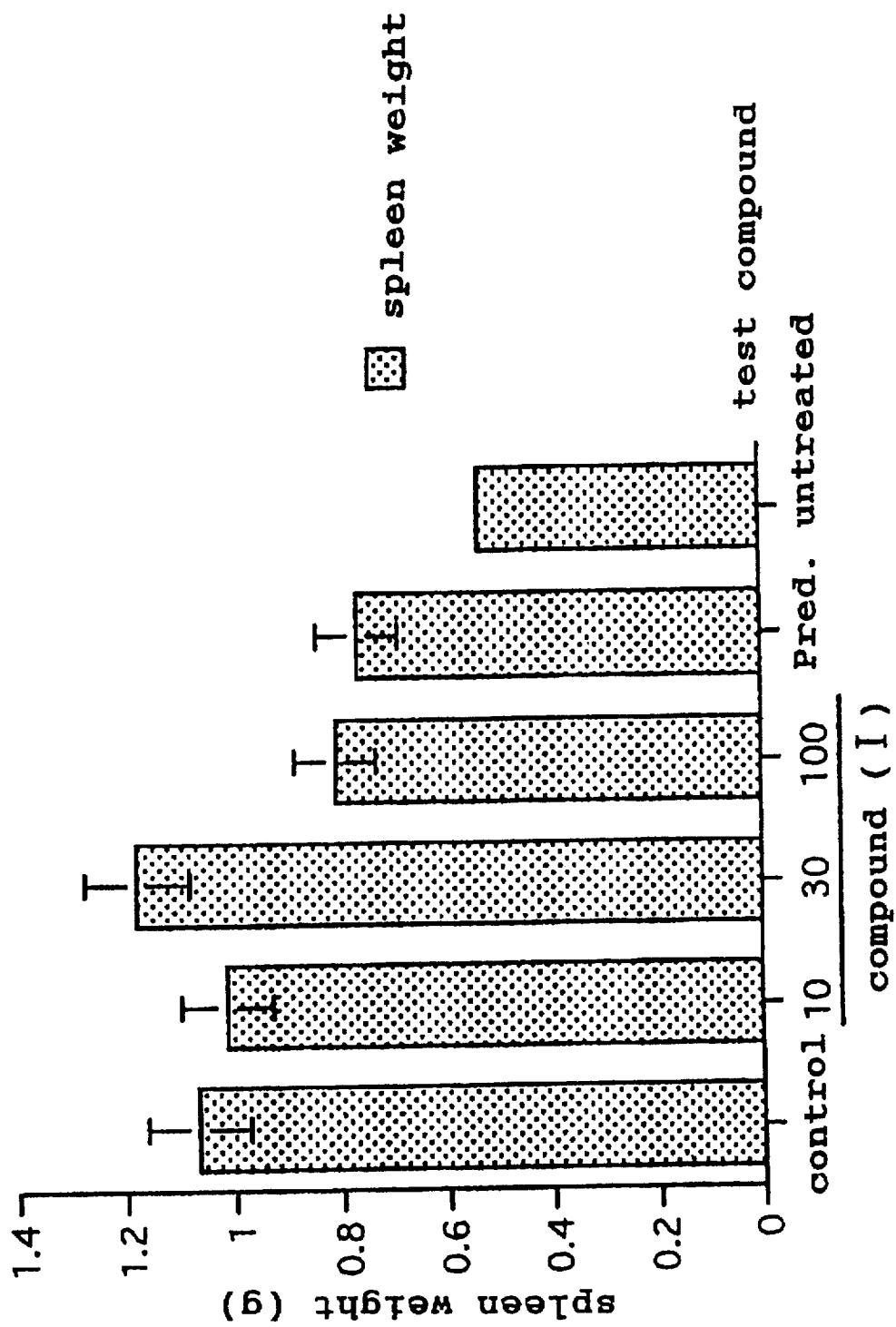
FIG. 8 is a graph comparing spleen weights among the group dosed with the compound of the present invention, the positive control group (prednisolone) and the control group (average ± standard error).
Figure 9:
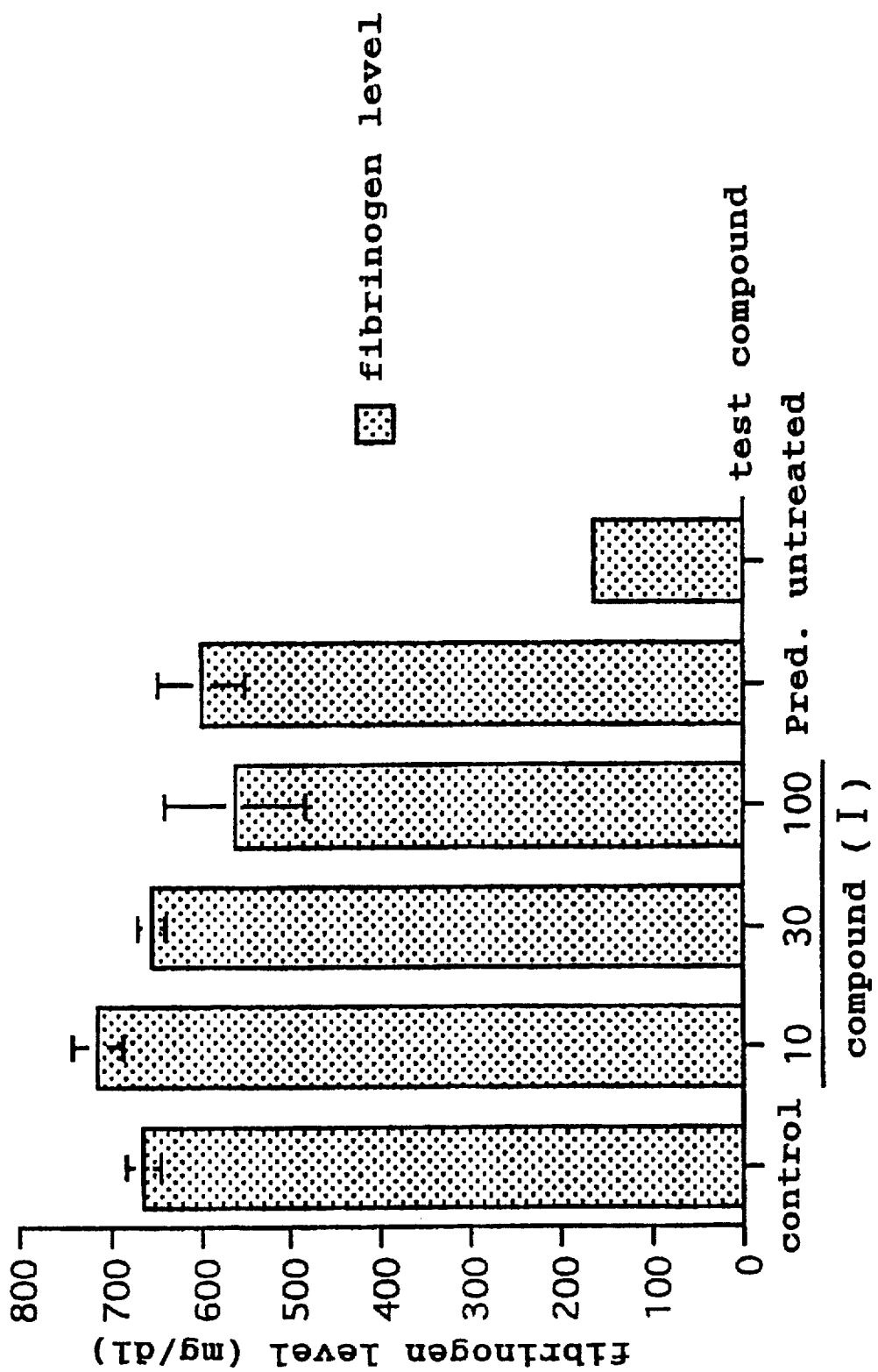
FIG. 9 is a graph comparing fibrinogen levels among the group dosed with the compound of the present invention, the positive control group (prednisolone) and the control group (average ± standard error).

2) Percentage volume increase (%) of untreated limb (refer to FIG. 2)

Test compd.

| week | control | compd.(I) [mg/Kg] 10 | 30 | 100 | Prednisolone 5 | untreated |
|---|---|---|---|---|---|---|
| 14 | 0.221 ± 0.062 | 0.298 ± 0.077 | 0.202 ± 0.047 | 0.241 ± 0.062 | 0.146 ± 0.056 | 0.115 ± 0.014 |
| 18 | 0.498 ± 0.090 | 0.561 ± 0.135 | 0.460 ± 0.079 | 0.210 ± 0.127 | 0.279 ± 0.106 | 0.109 ± 0.016 |
| 21 | 0.595 ± 0.063 | 0.597 ± 0.121 | 0.262 ± 0.071 | 0.240 ± 0.073 | 0.112 ± 0.052 | 0.042 ± 0.021 |

A clear edema suppressing effect was observed in the group in which the compound (I) was administered in a dose of 100 mg/kg.

On the final day (21st day), the suppressive effect was also recognized in the group in which the compound (I) was administered in a dose of 30 mg/kg (refer to FIGS. 1 and 2).

Figure 10:
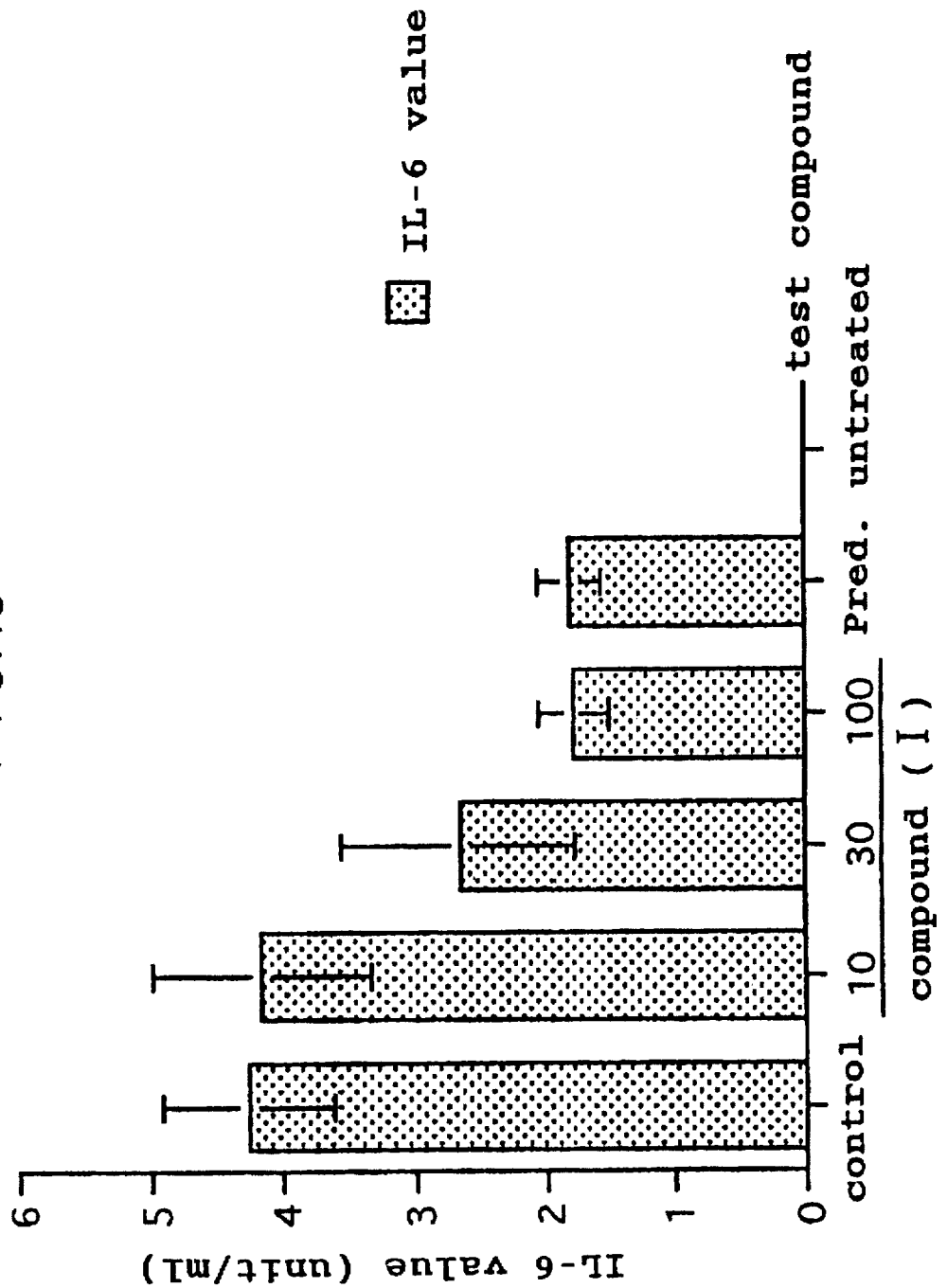
FIG. 10 is a graph comparing IL-6 values among the group dosed with the compound of the present invention, the positive control group (prednisolone) he control group (average ± standard error).

3) IL-6 (refer to FIG. 10)

Test compd.

| control | compd.(I) [mg/Kg] 10 | 30 | 100 | Prednisolone 5 | untreated |
|---|---|---|---|---|---|
| 4.268 ± 0.656 | 4.162 ± 0.831 | 2.660 ± 0.889 | 1.775 ± 0.282 | 1.809 ± 0.253 | 0 ± 0 |

Moreover, the compound (I) exhibited a dose-dependent suppressive effect on inflammatory cytokine IL-6 as well. In particular, the 100 mg/kg dosed group realized nearly the same suppression as the group dosed with 5 mg/kg of prednisolone (refer to FIG. 10).

Further, with respect to the acute phase reactive protein such as fibrinogen, no clear inhibitory effect was exhibited. With respect to the blood sedimentation, an inhibitory inclination was exhibited, which was, however, not a significant difference at all.

It is apparent from the above results that the compound of the present invention exerts excellent joint disease preventing, curing and ameliorating effects.

Toxicity Test Example (Experimental method)

(E)-3-[2-(5,6-Dimethoxy-3-methyl-1,4-benzoquinonyl)]-2-nonylpropenoic acid [compound (I)] was used as a test compound. (1) Rat:

250, 500, 1000 and 2000 mg/kg of the test compound were forcibly administered once to SD rat groups each consisting of three males and three females and they were observed for 14 days.

10, 20 and 60 (20 mg every one hour, 3 times) mg/kg of the test compound were forcibly administered once to SD rat groups consisting of five males and five females each and they were observed for 14 days. (2) Beagle:

100, 200 and 400 mg/kg of the test compound were forcibly administered once to beagle groups, each group consisting of one male and one female, and they were observed for 21 days. (Results)

The lethal dose to rat and beagle at single administration is given in the following Table.

| Animal sp. | Route of admin. | Lethal dose (mg/Kg) |
|---|---|---|
| rat | p.o. | 2000 |
| | i.v. | >60 |
| beagle | p.o. | >400 |

The excellent safety of the compound of the present invention is apparent from the above Table.

We claim:

1. A method of treating a joint disease associated with arthritis, comprising administering a pharmacologically effective amount of a quinone derivative represented by formula (I), or a pharmacologically acceptable salt thereof, to a person suffering from the joint disease associated with arthritis

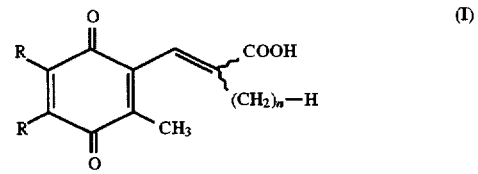

wherein n is 0 or an integer of 1 to 12 and R is a methyl or methoxy group.

2. The method claimed in claim 1, wherein the joint disease associated with arthritis is rheumatoid arthritis.

3. The method claimed in claim 1, wherein the quinone derivative (I) is (E)-3[2-(5,6-dimethoxy-3-methyl-1,4-benzoquinonyl)]-2-nonylpropenoic acid represented by formula (II):

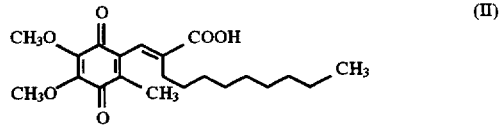

4. The method claimed in claim 3, wherein the joint disease associated with arthritis is rheumatoid arthritis.

5. A method of ameliorating the effects of a joint disease associated with arthritis in a subject comprising administering to the subject a pharmacologically effective amount of a quinone derivative represented by formula (I), or a pharmacologically acceptable salt thereof

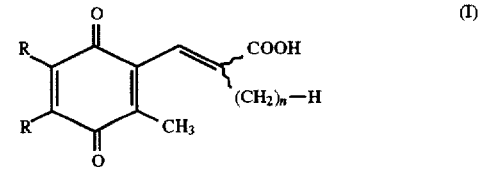

wherein n is 0 or an integer of 1 to 12 and R is a methyl or methoxy group.

* * * * *